US008409424B2

(12) United States Patent
Chen et al.

(10) Patent No.: US 8,409,424 B2
(45) Date of Patent: *Apr. 2, 2013

(54) ELECTROCHEMICAL TEST STRIP, ELECTROCHEMICAL TEST SYSTEM, AND MEASUREMENT METHOD USING THE SAME

(75) Inventors: Guan-Ting Chen, Tanzi Shiang (TW); Yueh-Hui Lin, Hsinchu (TW); Kai-Tsung Teng, Shalu Township (TW); Sz-Hau Chen, Taipei (TW); Thomas Y. S. Shen, Hsinchu (TW)

(73) Assignee: Apex Biotechnology Corp., Hsinchu (TW)

( * ) Notice: Subject to any disclaimer, the term of this patent is extended or adjusted under 35 U.S.C. 154(b) by 399 days.

This patent is subject to a terminal disclaimer.

(21) Appl. No.: 12/641,406

(22) Filed: Dec. 18, 2009

(65) Prior Publication Data

US 2010/0089775 A1 Apr. 15, 2010

Related U.S. Application Data

(63) Continuation-in-part of application No. 11/640,886, filed on Dec. 19, 2006, now Pat. No. 7,655,128.

(51) Int. Cl.
*G01N 27/327* (2006.01)
(52) U.S. Cl. ............. 205/792; 204/403.02; 204/403.04; 205/777.5
(58) Field of Classification Search ............ 204/403.01–403.15, 400; 205/777.5, 778, 792
See application file for complete search history.

(56) References Cited

U.S. PATENT DOCUMENTS 3,689,618 A * 9/1972 Chadwick .................. 264/104
5,582,697 A 12/1996 Ikeda et al.
5,651,869 A * 7/1997 Yoshioka et al. ........ 204/403.12
7,655,128 B2 * 2/2010 Hsu et al. .................. 205/775
2004/0256248 A1 * 12/2004 Burke et al. ............... 205/792
2007/0144918 A1 6/2007 Hsu et al.

FOREIGN PATENT DOCUMENTS

WO WO 2004/113910 A1 12/2004

OTHER PUBLICATIONS

European Search Report for European Patent Application No. 10015713.0 dated Jun. 4, 2011, pp. 1-6.

* cited by examiner

*Primary Examiner* — Alex Noguerola
(74) *Attorney, Agent, or Firm* — Ditthavong Mori & Steiner, P.C.

(57) ABSTRACT

An electrochemical test strip, an electrochemical test system, and a measurement method using the same are provided. The electrochemical test strip includes an insulating substrate, an electrode system formed on the insulating substrate, and an insulating layer formed on the electrode system. The electrode system includes a set of measurement electrodes, a set of identifying electrodes, and a resistive path having a predetermined resistance value. The set of identifying electrodes is made of metal material, and the resistive path is made of non-metal material. The set of measurement electrodes includes a reference electrode and a working electrode insulated from each other, and the set of identifying electrodes includes a first identifying electrode and a second identifying electrode connected with each other through the resistive path. The insulating layer covers a part of the electrode system, wherein a part of the electrode system not covered by the insulating layer forms a reaction region with a supply port. When a sample is injected into the supply port of the reaction region, the injected sample reaches the set of measurement electrodes and the set of identifying electrodes in sequence.

20 Claims, 5 Drawing Sheets

ELECTROCHEMICAL TEST STRIP, ELECTROCHEMICAL TEST SYSTEM, AND MEASUREMENT METHOD USING THE SAME

CROSS-REFERENCE TO RELATED APPLICATIONS

This application is a Continuation In Part (CIP) Application of U.S. application Ser. No. 11/640,886, filed Dec. 19, 2006, which is incorporated herein by reference in its entirety.

FIELD OF INVENTION

The present invention generally relates to an electrochemical test strip, an electrochemical test system, and a measurement method using the same, and more particularly, to an electrochemical test strip, an electrochemical test system, and a measurement method using the same capable of initiating a measurement instrument, determining if the test strip is inserted into a correct position of the measurement instrument, determining if the sample covers a reaction region of the test strip properly, and reducing measurement inaccuracy by using an AC measurement.

BACKGROUND OF THE INVENTION

The electrochemical test strips are widely employed in medical or biochemical test. The known electrochemical test strip has two electrodes for measuring the electrical characteristics of a sample after the sample being injected into a reaction region of the electrochemical test strip. However, in such structure, the electrochemical test strip cannot determine if the sample already covers two electrodes, and even cannot determine if the sample is injected into the reaction region.

To solve the above-mentioned problem, U.S. Pat. No. 5,582,697 disclosed an electrochemical test strip with three electrodes. U.S. Pat. No. 5,582,697 added a third electrode in the reaction region, and the third electrode is disposed farther from an entry of the reaction region than the other two electrodes. After injecting sample, the current variation between the electrode nearest to the entry and the electrode farthest from the entry is detected to determine if the sample appropriately covers the electrodes. To detect the sample, the test strip has to be inserted into an instrument and then electrically connected with the instrument. However, the method disclosed in U.S. Pat. No. 5,582,697 is unable to determine if the test strip is inserted into the instrument correctly, and is unable to determine if the sample is injected into the reaction region until the sample covers most part of the reaction region. In addition, these conventional methods were entirely based on the DC current alone, without considering the influence of AC electrical properties of the sample.

Accordingly, it is advantageous to have an electrochemical test strip capable of determining if it is inserted into a correct position of the instrument, testing the injection condition of the sample, and improving the measurement accuracy.

SUMMARY OF THE INVENTION

To solve the above-mentioned problems, the present invention provides an electrochemical test strip, a electrochemical test system, and a measurement method using the same capable of assisting in inserting the test strip into a correct position of an instrument, determining if the amount of sample being injected into the reaction region is sufficient, determining characteristics (such as viscosity, red blood cell count, hematocrit, total plate count, etc.) of the sample by utilizing an AC power module, and establishing different calibration parameters based on the characteristics of the sample to reduce the measurement errors.

According to an aspect of the present invention, an electrochemical test strip is provided. The electrochemical test strip includes an insulating substrate, an electrode system formed on the insulating substrate, and an insulating layer formed on the electrode system. The electrode system includes a set of measurement electrodes, a set of identifying electrodes, and a resistive path having a predetermined resistance value. The set of identifying electrodes is made of metal material, and the resistive path is made of non-metal material. The set of measurement electrodes includes a reference electrode and a working electrode insulated from each other, and the set of identifying electrodes includes a first identifying electrode and a second identifying electrode connected with each other through the resistive path. The insulating layer covers a part of the electrode system, wherein a part of the electrode system not covered by the insulating layer forms a reaction region with a supply port. When a sample is injected into the supply port of the reaction region, the injected sample reaches the set of measurement electrodes and the set of identifying electrodes in sequence.

According to another aspect of the present invention, an electrochemical test strip is provided. The electrochemical test strip includes an insulating substrate, an electrode system formed on the insulating substrate, and an insulating layer formed on the electrode system. The electrode system includes a first electrode, a second electrode, a third electrode, and a resistive path having a predetermined resistance value. The second and the third electrode are made of metal material, and the resistive path is made of non-metal material. The first electrode and the second electrode are insulated from each other, and the second electrode and the third electrode are connected with each other through the resistive path. The insulating layer covers a part of the electrode system, wherein a part of the electrode system not covered by the insulating layer forms a reaction region with a supply port. When a sample is injected into the supply port of the reaction region, the injected sample reaches the first electrode, the second electrode, and the third electrode in sequence. In one embodiment, the electrode system can further include a fourth electrode which is arranged such that when the sample is injected into the supply port of the reaction region, the sample reaches the first electrode, the fourth electrode, the second electrode, and the third electrode in sequence.

According to yet another aspect of the present invention, an electrochemical test system is provided. The electrochemical test system includes one of the above-mentioned electrochemical test strip and a measurement instrument. The measurement instrument includes a switch module, an analog-digital converter, an AC power module, a DC power module, an AC-DC power switch, a processor, and an insertion detector. The switch module is coupled to the electrode system and is configured to switch an electrical path between the electrode system and the measurement instrument. The analog-digital converter is couple to the switch module. The AC power module is configured to provide AC power, and DC power module is configured to provide DC power. The AC-DC power switch is coupled to the AC power module, the DC module, and the switch module, and is configured to selectively connect either the DC power module or the AC power module to the switch module. The processor is coupled to the analog-digital converter, the switch module, the DC power module, the AC power module, and the AC-DC power switch for controlling the operation thereof. The insertion detector is coupled to the switch module and the processor, and is configured to detect an electrical connection between the electrochemical test strip and the measurement instrument.

According to further another aspect of the present invention, a method for analyzing a sample using one of the above-mentioned electrochemical test strip is provided. The method includes the following steps: (a) inserting the electrochemical test strip into a measurement instrument to initiate the measurement instrument by forming a loop among the first identifying electrode, the resistive path, the second identifying electrode, and the measurement instrument; (b) providing the sample in the reaction region of the electrochemical test strip; (c) after providing the sample in the reaction region, applying an AC voltage between the first identifying electrode and the second identifying electrode, and measuring an AC electrical characteristic, such as a capacitance value or an AC impedance value, between the first identifying electrode and the second identifying electrode; (d) applying a DC voltage between the reference electrode and the working electrode, and measuring a current corresponding to the DC voltage; and (e) calibrating the measured current based on the measured AC electrical characteristic.

The objectives, embodiments, features, and advantages of the invention will be apparent from the following more particular description of preferred embodiments and drawings of the invention.

BRIEF DESCRIPTION OF THE PICTURES

The foregoing aspects and many of the attendant advantages of this invention will become more readily appreciated as the same becomes better understood by reference to the following detailed description, when taken in conjunction with the accompanying pictures, wherein.

DETAILED DESCRIPTION OF THE INVENTION

The present invention directs to an electrochemical test strip, an electrochemical test system, and a method for using the same. The present invention will be described more fully hereinafter with reference to the FIGS. 1-5. However, the devices, elements, and methods in the following description are configured to illustrate the present invention, and should not be construed in a limiting sense.

Figure 1:
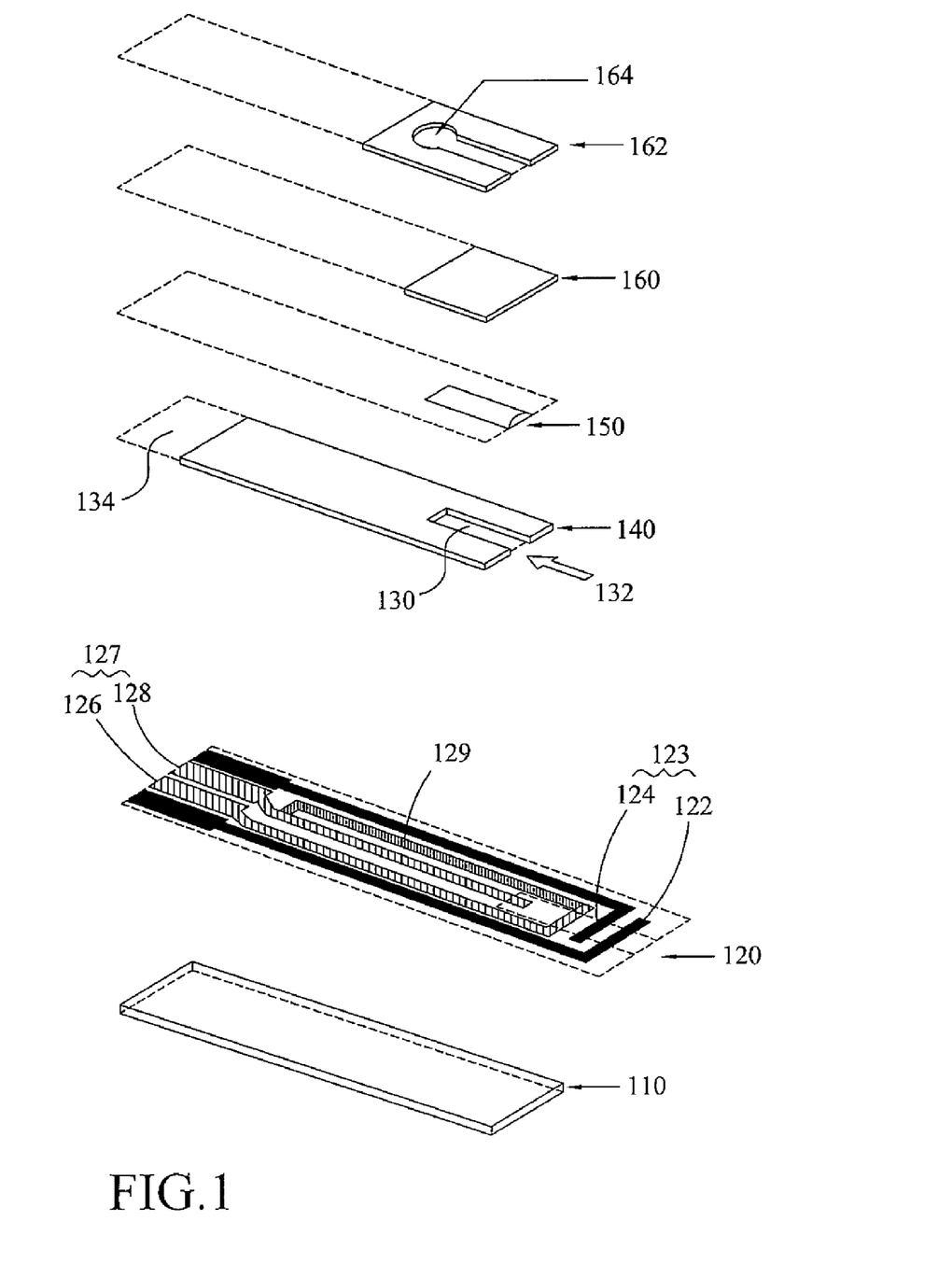
FIG. 1 shows a perspective view of an electrochemical test strip in accordance with an embodiment of the present invention.

FIG. 1 shows a perspective view of an electrochemical test strip in accordance with an embodiment of the present invention, in which the outline of the electrochemical test strip is plotted by dotted lines for comprehending the relative position among each element easily. The electrochemical test strip of the present invention includes an insulating substrate 110, an electrode system 120, an insulating layer 140, a hydrophilic layer 160, and a cover 162. The insulating layer 110 is electrically insulating and can be formed from a plate made of polyvinylchloride (PVC), glass fiber, polyester, bakelite, polyethylene terephthalate (PET), Polycarbonate (PC), polypropylene (PP), polyethylene (PE), polystyrene (PS), ceramic material or any other suitable material known in the art. The electrode system 120 includes a set of measurement electrodes 123, a set of identifying electrodes 127 and a resistive path 129, wherein the set of measurement electrodes 123 includes a reference electrode 122 and a working electrode 124 insulated from each other, and the set of identifying electrodes 127 includes a first identifying electrode 126 and a second identifying electrode 128 connected with each other through the resistive path 129. The material for the reference electrode 122 and the working electrode 124 can be any known conductive materials such as carbon paste, silver paste, copper paste, carbon/silver paste, or other similar material and the combination thereof. The first identifying electrode 126 and the second identifying electrode 128 are made of metal material, such as silver, gold, platinum, platinum, the alloy thereof, or the combination thereof. Further, the resistive path 129 is made of non-metal material, and preferably made of conductive non-metal material, such as carbon. Typically, the resistive path 129 has a predetermined resistance value which is usually larger than that of the sample to be tested.

The insulating layer 140 covers a part of the electrode system 120 so that a first part of the electrode system 120 not covered by the insulating layer 140 forms a reaction region 130 at one end for containing the sample, and a second part of the electrode system 120 not covered by the insulating layer 140 forms a connection region 134 at the other end. The reaction region 130 has a supply port 132 for injecting the sample. The material of the insulating layer 140 includes but not limited to PVC insulating tape, PET insulating tape, thermal drying insulating paint or ultraviolet drying insulating paint. When the sample is injected into the supply port 132 of the reaction region 130, the sample reaches the set of measurement electrodes 123 and the set of identifying electrodes 127 of the electrode system 120 in sequence.

The electrochemical test strip of the present invention further includes a reaction layer 150 disposed in the reaction region 130, which at least includes enzyme for reacting with the sample, and the type of the enzyme will vary with the sample to be tested, such as oxidoreductase or dehydrogenase. The reaction layer 150 covers at least the set of measurement electrodes 123 in the reaction region 130. The hydrophilic layer 160 and the cover 162 are arranged to form a vent hole 164 for discharging air in the reaction region 130, which enhances the capillary effect and facilitates the injection of the sample to shorten the time of filling the reaction region 130 with the sample. The hydrophilic layer 160 can conduct the flowing direction of the sample and has the function of discharging air.

After the electrochemical test strip is inserted into a measurement instrument, a loop is formed among the first identifying electrode 126, the second identifying electrode 128, and the measurement instrument through the resistive path 129, and then the measurement instrument is initiated. After the measurement instrument is initiated, a resistance value between the first identifying electrode 126 and the second identifying electrode 128 can be measured and compared with the resistance of the resistive path 129 to determine whether the electrochemical test strip is inserted into the measurement instrument properly.

After providing the sample into the electrochemical test strip, an electrical variation between the reference electrode 122 and the working electrode 124 caused by the sample is measured to determine whether the sample has been injected into the reaction region 130. In the reaction region 130, since the set of identifying electrodes 127 are positioned farther from the supply port 132 than the set of measurement electrodes 123, the sample has to cover the set of measurement electrodes 123 before it reaches the set of identifying electrodes 127. In other words, one can determine if the sample properly covers the set of measurement electrodes 123 by determining if the sample reaches the set of identifying electrodes 127. Therefore, after determining that the sample is injected into the reaction region 130, it can then determine whether the sample covers the reaction region 130 properly by measuring a resistance variation between the first identifying electrode 126 and the second identifying electrode 128. In the example of FIG. 1, the resistance value between the first identifying electrode 126 and the second identifying electrode 128 is the resistance value of the resistive path 129 before the sample is added, and will become about the same as the resistance value of the sample, assuming that the resistance value of the resistive path 129 is much larger than that of the sample, after the sample is added and reaches the set of the identifying electrodes 127.

After determining that the sample covers the reaction region 130 properly, an AC voltage measurement between the first identifying electrode 126 and the second identifying electrode 128 and a DC voltage measurement between the reference electrode 122 and the working electrode 124 can be performed, wherein the AC voltage measurement is intended to obtain a capacitance value and/or an AC impedance value of the sample for determining some characteristics of the sample, and the DC voltage measurement mainly measures the current variation caused by the chemical reaction between the sample and the enzyme of the reaction layer 150 in the reaction region 130. The current variation measured by the DC voltage measurement can be further calibrated according to the results of the AC voltage measurement.

Figure 2A:
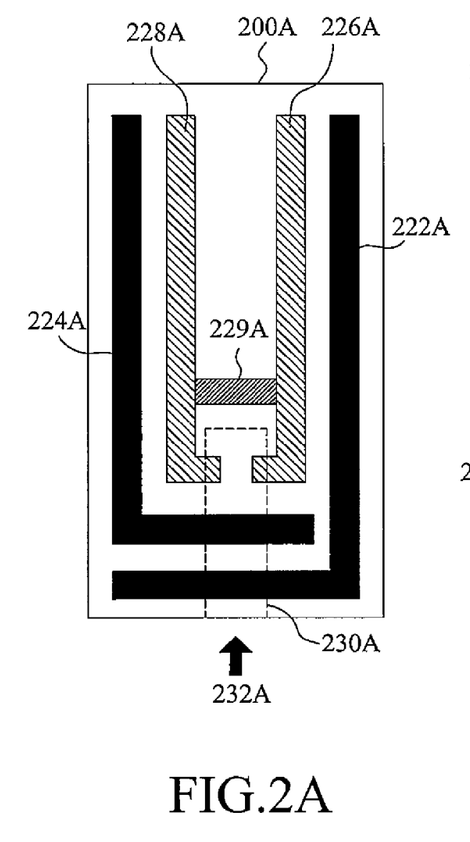
FIGS. 2A-2C illustrate three different electrode arrangements and configurations of reaction regions formed on the electrochemical test strip.
Figures 2B, 2C:
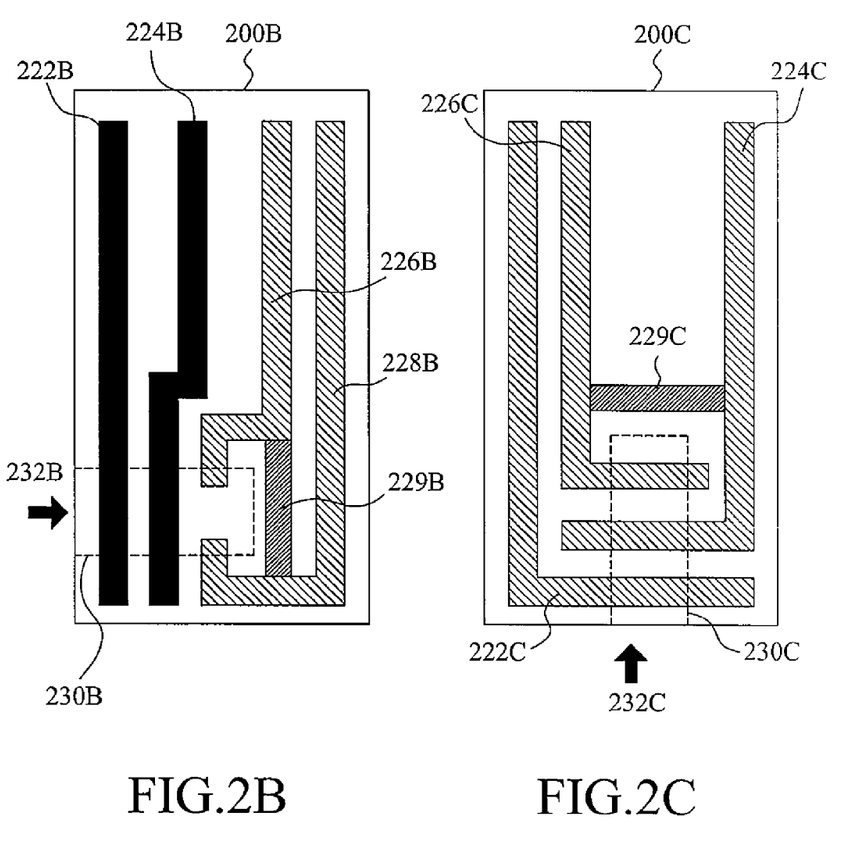

FIGS. 2A-2C illustrate three kinds of electrode arrangements and configurations of the reaction region formed on the electrochemical test strip. Referring to FIG. 2A, on the electrochemical test strip 200A, the reference electrode 222A and the working electrode 224A are insulated from each other, and the first identifying electrode 226A and the second identifying electrode 228A are separated from each other but connected through the resistive path 229A. In FIG. 2A, the supply port 232A of the reaction region 230A is on the underside. Referring to FIG. 2B, on the electrochemical test strip 200B, the reference electrode 222B and the working electrode 224B are insulated from each other, and the first identifying electrode 226B and the second identifying electrode 228B are separated from each other but connected through the resistive path 229B. In FIG. 2B, the supply port 232B of the reaction region 230B is on the left side. As illustrated in FIGS. 2A and 2B, the reference electrode, the working electrode, and the identifying electrodes are arranged in sequence from the supply port of the reaction region. Actually, as long as the electrodes in the reaction region are arranged in the order described above, the present invention does not limit the arrangement of the electrodes and the configuration of the reaction region. For example, in the embodiment shown in FIG. 2C, a first electrode 222C, a second electrode 224C, a third electrode 226C, and a resistive path 229C are formed on the electrochemical test strip 200C, wherein the first electrode 222C is insulated from both of the second electrode 224C and the third electrode 226C, while the second electrode 224C and the third electrode 226C are separated from each other but connected through the resistive path 229C. When the sample is injected into the supply port 232C of the reaction region 230C, the sample reaches the first electrode 222C, the second electrode 224C, and the third electrode 226C in sequence. In this embodiment, the first electrode 222C, the second electrode 224C, and the third electrode 226C are made of metal material, and the resistive path 229C is made of conductive non-metal material. The function of the pair of the first electrode 222C and the second electrode 224C is similar to that of the set of measurement electrodes 123 shown in FIG. 1, and the function of the pair of the second electrode 224C and the third electrode 226C is similar to that of the set of identifying electrodes 127 shown in FIG. 1. In other words, the second electrode 224C can be considered as a dual-function electrode which can act either as the working electrode 124 or as the first identifying electrode 126.

Figure 3:
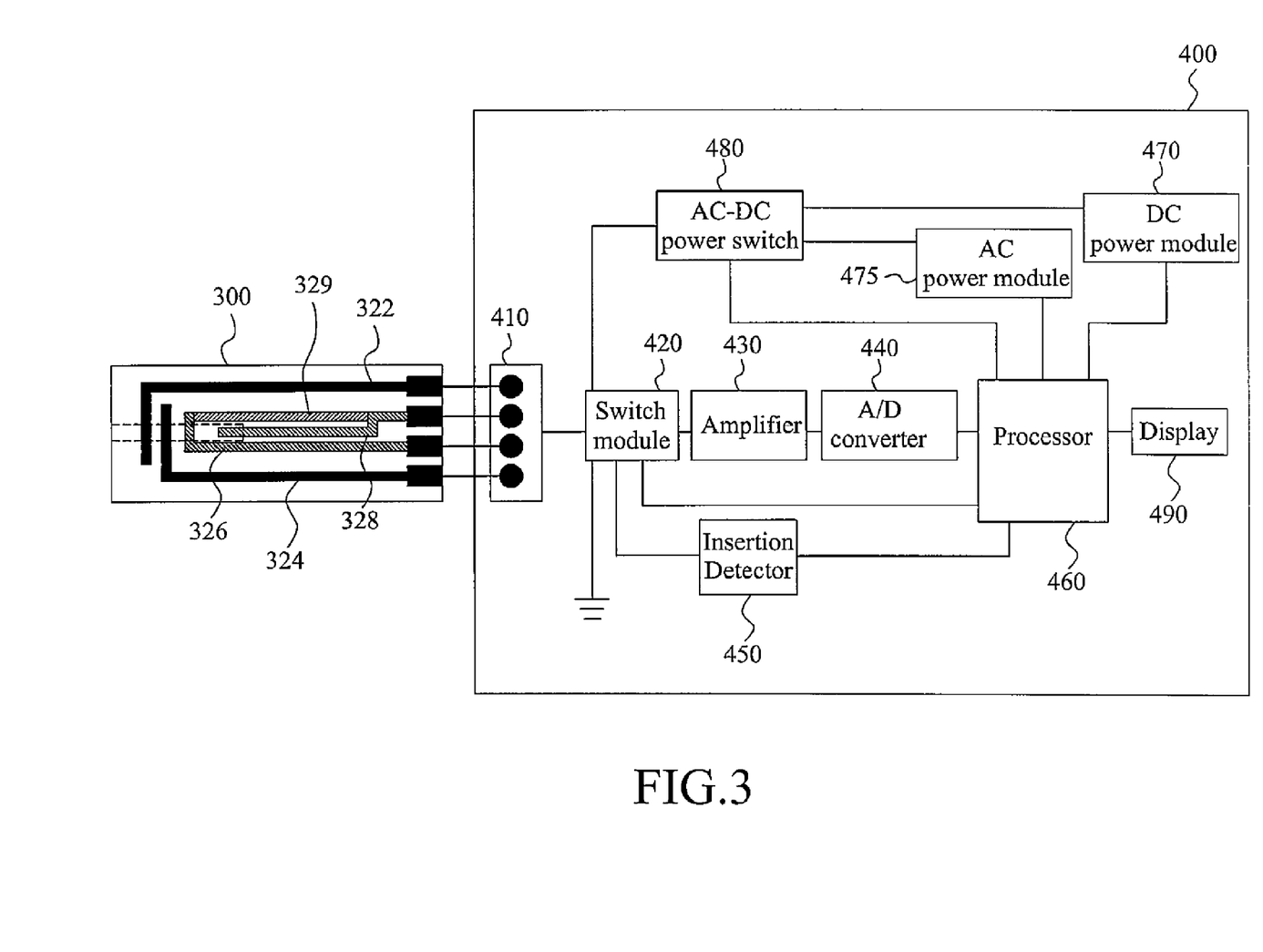
FIG. 3 shows a block diagram of an electrochemical test system in accordance with an embodiment of the present invention.

FIG. 3 shows a block diagram of an electrochemical test system in accordance with an embodiment of the present invention, which includes an electrochemical test strip 300 and a measurement instrument 400. In this embodiment, the structure and the components of the electrochemical test strip 300 are similar to that of the electrochemical test strip 100 in FIG. 1. The measurement instrument 400 includes connector 410 for external connection, a switch module 420, an amplifier 430, an analog-digital converter 440, an insertion detector 450, a processor 460, a DC power module 470, an AC power module 475, and an AC-DC power switch 480. The reference electrode 322, the working electrode 324, the first identifying electrode 326, and the second identifying electrode 328 of the electrochemical test strip 300 are electrically connected to the measurement instrument 400 through the connector 410. The switch module 420, coupled to the connector 410, is configured to switch an electrical path between the electrodes of the electrochemical test strip 300 and the measurement instrument 400. In one embodiment, the switch module 420 can selectively connect the electrodes of the electrochemical test strip 300 to a ground point or to the circuits within the measurement instrument 400. The DC power module 470 and the AC power module 475 are configured to provide DC power and AC power respectively. The AC-DC power switch 480, coupled to the DC power module 470, the AC power module 475, and the switch module 420, is configured to selectively connect either the DC power module 470 or the AC power module 475 to the switch module 420. Typically, the states of the switch module 420 and the AC-DC power switch 480 are controlled by the processor 460. The measurement instrument 400 further includes a display 490 for displaying the measurement result. In another embodiment of the present invention, the display 490, the DC power module 470, and/or the AC power module 475 can be external devices, not included in the measurement instrument 400.

When the electrochemical test strip 300 is connected to the connector 410, a loop is formed among the first identifying electrode 326, the resistive path 329, the second identifying electrode 329, the connector 410, the switch module 420 and the insertion detector 450, whereby a signal is transmitted to the processor 460 to initiate the measurement instrument 400. The insertion detector 450 can be a known power-on circuit which is an open circuit before the insertion of the test strip 300 and becomes a loop after the insertion of the test strip 300. For example, the insertion detector 450 can include a diode or a transistor that will be turned on after the insertion of the test strip 300, and the caused voltage variation in an anode of the diode or in a collector of the transistor can initiate the measurement instrument 400. However, in some situations, other unexpected factors may also initiate the measurement instrument 400. Therefore, the processor 460 can determine if the electrochemical test strip 300 is connected with the connector

410 properly by providing a DC voltage between the first identifying electrode 326 and the second identifying electrode 328 after the measurement instrument 400 is initiated, and then measuring a resistance value corresponding to the DC voltage and comparing it with the resistive path 329.

After determining that the electrochemical test strip 300 is connected with the connector 410 properly, a DC voltage can be applied between the reference electrode 322 and the working electrode 324 under the control of the processor 460. The resistance between the reference electrode 322 and the working electrode 324 will change after the sample is injected into the reaction region of the electrochemical test strip 300. Generally, the resistance is reduced because the sample connects the reference electrode 322 and the working electrode 324. Next, the resistance variation is digitalized by the amplifier 430 and the analog-digital converter 440 and then transmitted to the processor 460, which allows the processor 460 to determine if the sample is injected into the reaction region.

After determining that the sample is injected into the reaction region, the distribution of the sample in the reaction region can be detected by measuring a resistance value between the first identifying electrode 326 and the second identifying electrode 328. If the sample doesn't contacts with the first identifying electrode 326 and the second identifying electrode 328, the measured resistance value is about equal to the resistance value of the resistive path 329. On the other hand, once the sample reaches both of first identifying electrode 326 and the second identifying electrode 328 which are positioned at the far end of the reaction region, the measured resistance value will decrease considerably, whereby the processor 460 can determine that the sample covers the reaction region appropriately.

After determining that the sample covers the reaction region properly (i.e. the sample covers the reference electrode 322 and working electrode 324 completely), the processor 460 can apply an AC voltage between the first identifying electrode 326 and the second identifying electrode 328, by controlling the AC-DC power switch 480 to switch on the path of the AC power module 475 and switch off the path of the DC power module 470, to measure a capacitance value and/or an AC impedance value of the sample. Next, the processor 460 can apply a DC voltage between the reference electrode 322 and the working electrode 324, by controlling the AC-DC power switch 480 to switch on the path of the DC power module 470 and switch off the path of the AC power module 475, to measure a current variation caused by the chemical reaction between the sample and the reaction layer placed in the reaction region. The measured current variation can be further calibrated according to the measured capacitance value (and/or the AC impedance value) of the sample.

Figure 4:
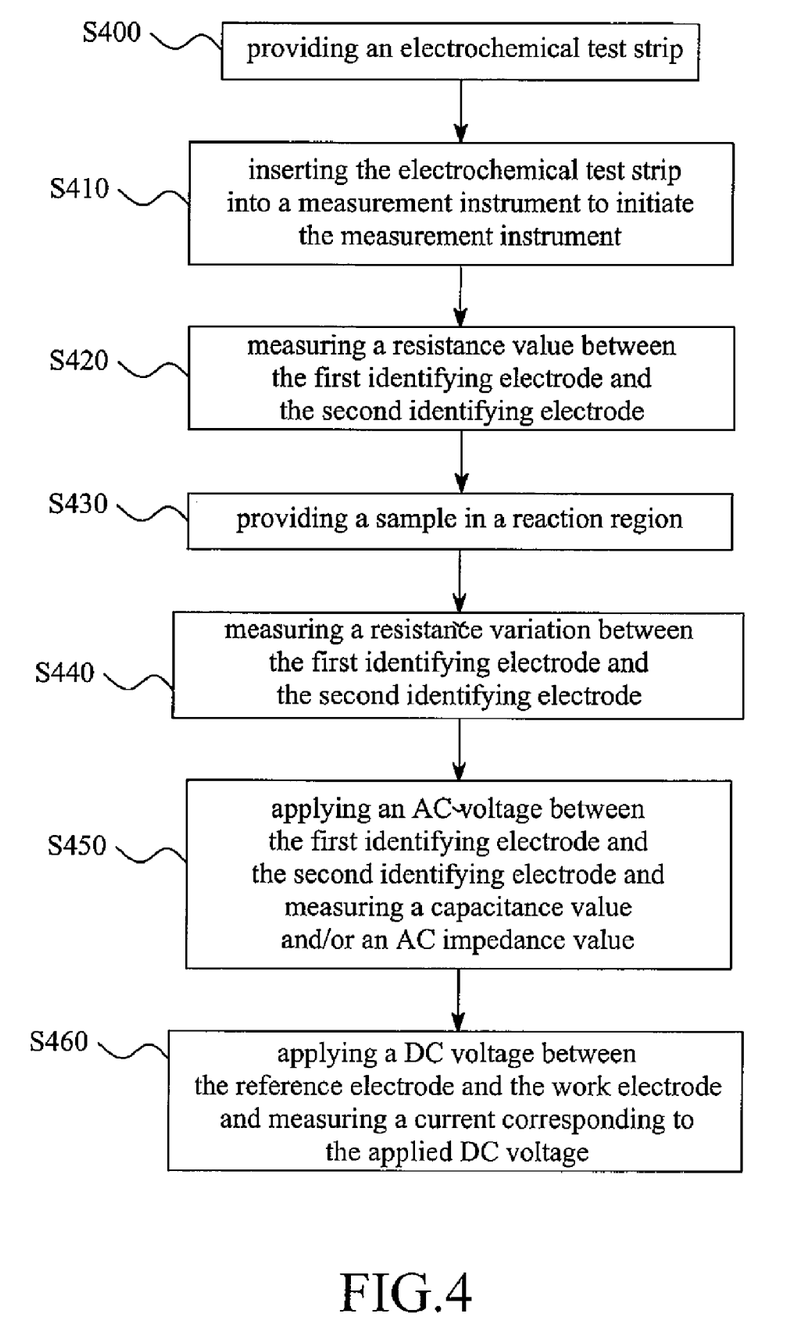
FIG. 4 is a flowchart showing the procedure of testing a sample by using an electrochemical test strip of the present invention.

FIG. 4 is a flowchart showing the procedure of a method for analyzing a sample by using an electrochemical test strip of the present invention. First, in step S400, the electrochemical test strip of the present invention is provided. As described above, the test strip cam include four electrodes: a reference electrode, a working electrode, a first identifying electrode, and a second identifying electrode, wherein the reference electrode and the working electrode are insulated from one another, and the first identifying electrode and the second identifying electrode are connected with each other through a resistive path, as shown in FIG. 1. In another embodiment, the test strip may include three electrodes as shown in FIG. 2C. In the following, the test strip shown in FIG. 1 is used to illustrate the method of the present invention. In step S410, the electrochemical test strip is inserted into a measurement instrument to initiate the measurement instrument. After the instrument is initiated, in step S420, a resistance value between the first identifying electrode and the second identifying electrode is measured. If the resistance corresponds to an expected value (typically, the resistance value of the resistive path), the procedure proceeds to step S430, and a sample is provided in a reaction region of the electrochemical test strip. Next, in step S440, a resistance variation between the first identifying electrode and the second identifying electrode is measured, which may indicate that the sample covers the reaction region properly if the resistance variation is within an expected range. For example, if the measurement result of step S440 shows a sufficient variation as compared with the resistance measured in step S420, it is determined that the sample covers the reaction region properly. In another embodiment, before performing the step S440, the method can further include a step of measuring a resistance between the reference electrode and the working electrode to determine whether the sample is injected into the reaction region. After determining that the sample appropriately covers the reaction region, the procedure proceeds to step S450 to apply an AC voltage between the first identifying electrode and the second identifying electrode to measure a capacitance value and/or an AC impedance value of the sample. Typically, some characteristic of the sample, such as viscosity, red blood cell count, hematocrit, total plate count, can be determined according to the measured capacitance value and the AC impedance value. Furthermore, based on these characteristics of the sample, the calibration parameters can be established for calibration of the DC measurement. Next, in step S460, a DC voltage is applied between the reference electrode and the work electrode to measure a current corresponding to the applied DC voltage, and then the measured current is calibrated according to the above-described calibration parameters.

Figure 5:
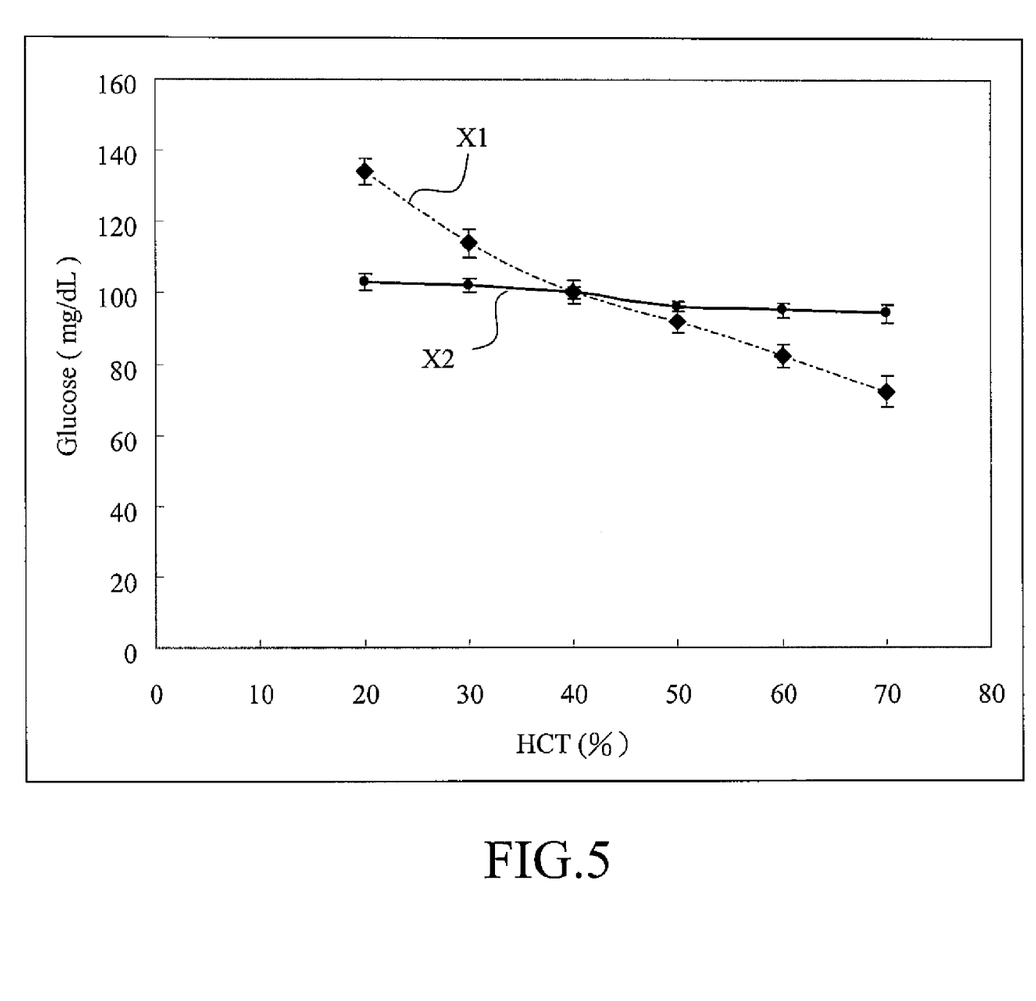
FIG. 5 shows measurement results of blood glucose concentrations of five blood samples to illustrate the difference between the methods of prior art and the present invention.

FIG. 5 shows measurement results of blood glucose to illustrate the difference between the methods of prior art and the present invention. In this embodiment, five blood samples are measured by both the prior art method and the present method, wherein the five blood samples have the same blood glucose concentration of about 100 mg/dL, but have different HCT (Hematocrit) levels of 20%, 30%, 40%, 50%, 60%, and 70%. It can be seen that measurement results obtained by the prior art method, represented by the curve X1, are adversely affected by the level of HCT. For example, the measured concentration of the blood glucose of the sample with 30% HCT is 14% larger than that of the sample with 40% HCT. Furthermore, both of the measured blood glucose concentrations of the sample with 20% HCT and the sample with 70% HCT are up to 20% larger than that of the sample with 40% HCT. Therefore, the influence of HCT level on measurement accuracy of blood glucose concentration is of significance. In order to diminish the measurement error caused by the level of HCT, the present invention uses an AC voltage measurement to detect the HCT level of blood sample before performing measuring the blood glucose concentration of the sample. Typically, based on the results of the AC voltage measurement, calibration parameters can be established for calibrating the concentration measurement. Referring to FIG. 5, curve X2 represents the measurement results calibrated by the calibration parameters obtained through the AC voltage measurement, which shows that the measurement error can be controlled within 5%. Therefore, it can be seen that the method of the present invention can effectively remove the effect of HCT level on the blood glucose concentration measurement.

Although the specific embodiments of the present invention have been illustrated and described, it is to be understood that the invention is not limited to those embodiments. One skilled in the art may make various modifications without departing from the scope or spirit of the invention.

The invention claimed is:

1. An electrochemical test strip, comprising:
   an insulating substrate;
   an electrode system formed on the insulating substrate, the electrode system comprising a set of measurement electrodes, a set of identifying electrodes and a resistive path having a predetermined resistance value, wherein the set of identifying electrodes is made of metal material and the resistive path is made of non-metal material, wherein the set of measurement electrodes comprises a reference electrode and a working electrode insulated from each other, and the set of identifying electrodes comprises a first identifying electrode and a second identifying electrode connected with each other through the resistive path; and
   an insulating layer covering a part of the electrode system, wherein a part of the electrode system not covered by the insulating layer forms a reaction region with a supply port;
   wherein when the sample is injected into the supply port of the reaction region, the sample reaches the set of measurement electrodes and the set of identifying electrodes in sequence.

2. The electrochemical test strip of claim 1, further comprising a cover disposed on the insulating layer, the cover comprising a vent hole for discharging air in the reaction region.

3. The electrochemical test strip of claim 1, further comprising a reaction layer disposed on the reaction region, wherein the reaction layer comprises an enzyme.

4. The electrochemical test strip of claim 1, wherein the set of identifying electrodes is made of silver, gold, or platinum, and the resistive path is made of carbon.

5. An electrochemical test system, comprising:
   the electrochemical test strip of claim 1; and
   a measurement instrument, comprising:
      a switch module coupled to the electrode system and configured to switch an electrical path between the electrode system and the measurement instrument;
      an analog-digital converter coupled to the switch module;
      an AC power module configured to provide AC power;
      a DC power module configured to provide DC power;
      an AC-DC power switch coupled to the AC power module, the DC module, and the switch module, and configured to respectively connect the DC power module and the AC power module to the switch module;
      a processor coupled to the analog-digital converter, the switch module, the DC power module, the AC power module, and the AC-DC power switch, and configured to control the switch module, the DC power module, the AC power module, and the AC-DC power switch, wherein the processor applies an AC voltage between the set of identifying electrodes and applies a DC voltage between the set of measurement electrodes simultaneously; and
      an insertion detector coupled to the switch module and the processor, and configured to detect an electrical connection between the electrochemical test strip and the measurement instrument.

6. The electrochemical test system of claim 5, wherein the DC power module applies a DC voltage between the first identifying electrode and the second identifying electrode before and after the sample is injected into the reaction region to measure a resistance variation between the first identifying electrode and the second identifying electrode.

7. The electrochemical test system of claim 5, wherein the AC power module applies an AC voltage between the first identifying electrode and the second identifying electrode after the sample is injected into the reaction region of the electrochemical test strip to measure a capacitance value or an AC impedance value between the first identifying electrode and the second identifying electrode.

8. The electrochemical test system of claim 5, wherein the DC power module applies a DC voltage between the reference voltage and the working electrode after the sample is injected into the reaction region, and a current corresponding to the DC voltage is transmitted to the processor through the switch module and the analog-digital converter.

9. The electrochemical test system of claim 5, wherein the measurement instrument further comprises a display coupled to the processor and configured to display an electrical variation of the electrode system.

10. A method for analyzing a sample using the electrochemical test strip of claim 1, comprising:
    (a) inserting the electrochemical test strip into a measurement instrument to initiate the measurement instrument by forming a loop among the first identifying electrode, the resistive path, the second identifying electrode, and the measurement instrument;
    (b) providing the sample in the reaction region of the electrochemical test strip;
    (c) after providing the sample in the reaction region, applying an AC voltage between the first identifying electrode and the second identifying electrode, and measuring a capacitance value or an AC impedance value between the first identifying electrode and the second identifying electrode; and
    (d) applying a DC voltage between the reference electrode and the working electrode, and measuring a current corresponding to the DC voltage.

11. The method of claim 10, further comprising the following step between the step (a) and the step (b):
    (a1) before providing the sample in the reaction region, measuring a first resistance value between the first identifying electrode and the second identifying electrode to determine whether the electrochemical test strip is inserted into the measurement instrument properly.

12. The method of claim 11, further comprising the following step between the step (b) and the step (c):
    (b1) after providing the sample in the electrochemical test strip, measuring a second resistance value between the first identifying electrode and the second identifying electrode; and
    determining whether the sample covers the reference electrode and the working electrode by comparing the first resistance value and the second resistance value.

13. The method of claim 10, wherein the step (c) further comprises determining characteristics of the sample according to the capacitance value or the AC impedance value, wherein the characteristics of the sample comprises viscosity, red blood cell count, hematocrit, total plate count, or the combination thereof.

14. The method of claim 13, further comprising the following step after the step (d):
    calibrating the current according to the characteristics of the sample.

15. The method of claim 10, wherein the loop causes a voltage variation either in an anode of a diode by turning on the diode or in a collector of a transistor by turning on the transistor, and the voltage variation initiates the measurement instrument.

16. An electrochemical test strip, comprising:

an insulating substrate;

an electrode system formed on the insulating substrate, the electrode system comprising a first electrode, a second electrode, a third electrode, and a resistive path having a predetermined resistance value, wherein the second and the third electrode are made of metal material and the resistive path is made of non-metal material, wherein the first electrode and the second electrode are insulated from each other, and the second electrode and the third electrode are connected with each other through the resistive path; and an insulating layer covering a part of the electrode system, wherein a part of the electrode system not covered by the insulating layer forms a reaction region with a supply port;

wherein when the sample is injected into the supply port of the reaction region, the sample reaches the first electrode, the second electrode, and the third electrode in sequence.

17. The electrochemical test strip of claim 16, further comprising a fourth electrode insulated from the first electrode, the second electrode, and the third electrode, and wherein when the sample is injected into the supply port of the reaction region, the sample reaches the first electrode, the fourth electrode, the second electrode, and the third electrode in sequence.

18. The electrochemical test strip of claim 16, further comprising a cover disposed on the insulating layer, the cover comprising a vent hole for discharging air in the reaction region.

19. The electrochemical test strip of claim 16, further comprising a reaction layer disposed on the reaction region, wherein the reaction layer comprises an enzyme.

20. The electrochemical test strip of claim 16, wherein the second and the third electrode are made of silver, gold, or platinum, and the resistive path is made of carbon.

* * * * *